United States Patent [19]

Bro

[11] 4,354,504
[45] Oct. 19, 1982

[54] THERMAL DIFFUSION FLOW PROBE

[76] Inventor: William J. Bro, 3735 W. Cavalier Dr., Phoenix, Ariz. 85019

[21] Appl. No.: 72,148

[22] Filed: Sep. 4, 1979

[51] Int. Cl.³ .............................................. A61B 5/02
[52] U.S. Cl. ...................... 128/691; 128/736; 73/190 H; 73/204
[58] Field of Search ............... 128/691, 692, 713, 736; 73/190 H, 204

[56] References Cited

U.S. PATENT DOCUMENTS

| | | | |
|---|---|---|---|
| 2,982,132 | 5/1961 | Mendlowitz | 128/691 |
| 3,789,831 | 2/1974 | Kopaniky et al. | 128/692 |
| 3,933,149 | 1/1976 | Salera | 128/736 |
| 4,198,859 | 4/1980 | Holtermann | 73/190 H |

FOREIGN PATENT DOCUMENTS

| | | | |
|---|---|---|---|
| 271100 | 6/1965 | Australia | 128/736 |
| 1033741 | 6/1966 | United Kingdom | 128/692 |
| 127358 | 7/1967 | U.S.S.R. | 128/736 |
| 271043 | 8/1970 | U.S.S.R. | 73/204 |
| 556786 | 7/1977 | U.S.S.R. | 128/691 |

OTHER PUBLICATIONS

Carter et al., "Regional Cortical Blood Flow", Neurosurgery, vol. 2, No. 3, 1978, pp. 223-229.

Primary Examiner—Lee S. Cohen
Attorney, Agent, or Firm—Gregory J. Nelson

[57] ABSTRACT

A blood-flow probe utilizing two-terminal integrated circuit temperature transducers each of which produces an output current proportional to the absolute temperature of the probe contact plate with which the temperature transducer is associated. One such temperature transducer monitors the temperature of the cold plate of the probe. The other temperature transducer monitors that of the hot plate. Each transducer output signal is carried from the probe so that the temperature of the hot plate and of the cold plate may be independently measured. The hot plate temperature is monitored and maintained at a safe level so as not to endanger the patient by causing tissue damage.

25 Claims, 3 Drawing Figures

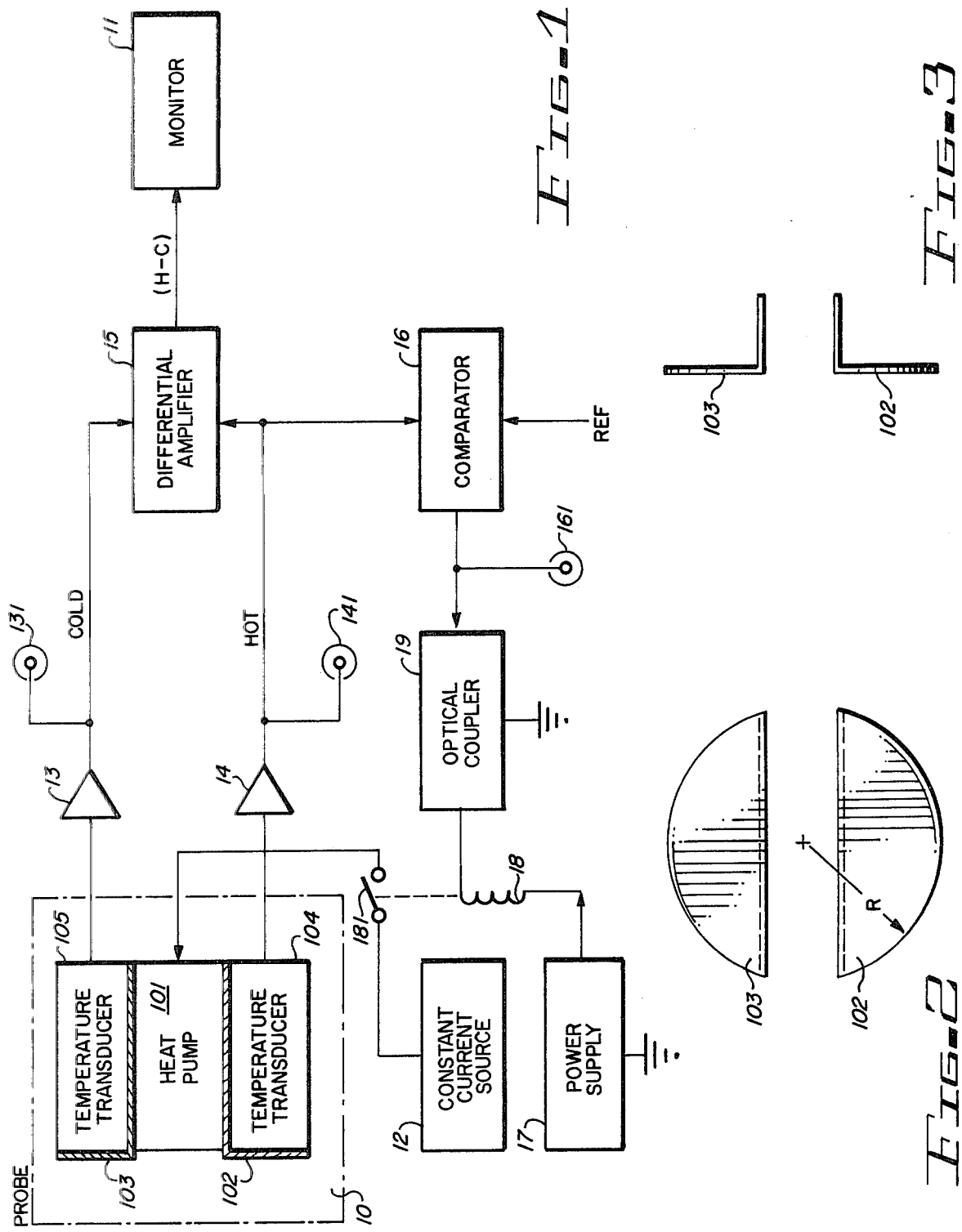

THERMAL DIFFUSION FLOW PROBE

FIELD OF THE INVENTION

The invention is related to the field of internal calorimetry.

More particularly, the invention relates to the use of internal calorimetry for the determination of blood flow in bodily structures.

Even more particularly, the invention relates to the use of internal calorimetry to assess regional blood flow at the surgery site during the surgical treatment of cerebrovascular diseases.

PRIOR ART

In the "Proceedings of the Society of Experimental Biology", N.N., Vol. 31 pg. 141 (1933), F. A. Gibbs disclosed a versatile blood-flow recorder comprising a heated thermocouple. Although Gibbs blood-flow recorder was originally intended for the measurement of blood-flow changes in arteries and veins, it was frequently used for the measurement of vascular changes in internal organs. An iron-constantan thermocouple was imbedded in the body tissue being investigated. A constant current was passed through the constantan filament so that the temperature recorded by the thermocouple was higher than that of the afferent blood. A subsequent increase in blood flow caused the relatively hot thermocouple to cool. Conversely, a decrease in blood flow permitted the thermocouple to increase in temperature. The variations in the temperature of the thermocouple may thus be directly related to the blood-flow in the tissue being monitored. In 1934 in the American Journal of Physiology, Vol. 108 pg, 201, C. F. Schmidt and J. C. Pierson reported on the use of the Gibbs blood-flow recorder for monitoring blood-flow of the brain.

While the application of Gibbs blood-flow recorder provided significant experimental data, the results obtained were purely qualitative. J. Grayson of the Department of Physiology at the University of Bristol undertook to achieve quantative results by adopting Gibbs blood flow recorder to his own purposes. He designated the methods derived as those of "internal calorimetry" based on the fact that the fundamental measurement obtained is one of heat transfer in internal organs. He reported his results in the Journal of Physiology. In Vol. 114 at pg. 29 he reported that when a heated thermocouple is used to monitor blood-flow of an organ, heat is lost partly by direct conduction to the tissues and partly to be blood circulating through those tissues. In Vol. 118 at pgs. 54–72 he reports on experiments which show that for any given increment of temperature change at the thermocouple, in any given bodily tissue, the conductivity losses to the tissues are constant and the circulatory losses from the heated thermocouple are a linear function of blood-flow; are easily measured; and provide a useful quantitative index of blood-flow.

Doctors Carter and Atkinson of the neurosurgical research laboraty, Barrow Neurological Institute of St. Joseph's Hospital and Medical Center, Phoenix, Arizona reported on the use of thermodiffusion techniques in the measurement of cortical blood-flow in controlled hypotension, in a paper presented before the Western Neurosurgical Society at Colorado Springs on Nov. 2, 1971. They adopted a thermodiffusion probe first described by Brawley (Scan J Clin Lab Invest 13 B, Supplement 102, 1968). Brawley used a thermoelectric heat pump (Peltier stack) in a thermodiffusion probe to create one heated and one cooled plate. In use, the difference in temperature between the two plates varied with cortical blood-flow. Ideally, ambient temperature variations would not affect the incremental difference existing between the two plates.

The probe utilized by Carter and Atkinson was a modification of that of Brawley. They used a peltier device with bell shaped gold contact plate. Copper constantine thermocouples were spot welded at the approximate center of the back of these gold plates and were connected with opposite polarity so the output of the thermocouple pair would be zero when each plate was at the same temperature. The L-shaped gold plates provided the cerebral contact surfaces. They found the temperature differences between the plates varied with cortical blood-flow and, in vitro tests, no significant changes in temperature gradient occurred between the two plates thus demonstrating the probes independence of the ambient cortical temperature. The probe demonstrated a response time constant of 4.2 seconds.

Animal experiments were used to establish a dead brain or zero blood flow value for the probe. The probe was then calibrated by correlation with $^{133}$xe diffusion-washout curves obtained in animal experiments. This procedure involves the injection of $^{133}$xe into the brachiocethalic artery followed rapidly by a saline flush. The probe correlation was obtained by monitoring both the cortical blood-flow as indicated by the probe while simultaneously recording the $^{133}$xe diffusion-washout curves. These experiments noted a quasi-linear relationship between cortical blood-flow as measured by the $^{133}$xe diffusion-washout and by the diffusion flow probe. The correlation of the cortical blood-flow as measured with the Peltier Flow Probe and the $^{133}$xe radioactive diffusion-washout indicates that the probe provides quantitative and reproducible results from one experiment to the next. Of significant importance is the fact that acute changes in blood flow are noted almost immediately, within the 4.2 second response time constant of the Peltier Probe. The significance of this is realized when one reflects that it takes only three minutes to damage tissue as a result of blood-flow restriction whereas it takes at least fifteen minutes to run a radioactive diffusion-washout test. Further, such diffusion-washout tests may not be repeated any sooner than fifteen minutes after completion of a prior washout test. Thus the 4.2 second response time of the Peltier Flow Probe provides a near real time record of regional cortical flow during an operative procedure.

Despite the advantages of the Peltier Flow Probe, there is a hidden danger associated with its use in cortical egions. Should the hot plate temperature exceed 42° C. damage to the tissues can result. Carter and Atkinson in their 1971 paper appear to indicate that hot plate temperatures at least as high as 40.25° C. were achieved during the course of their experimentation. No precautions appear to have been made to prevent the hot plate temperature from exceeding the critical 42° C.

It is therefore an object of the present invention to provide a blood-flow probe having as a primary design criterion the safety of the patient.

It is a further objective of the invention to provide a probe which will be constructed so as to be capable of being placed safely in contact with exposed organs and tissues of a patient without damaging those organs or tissue or causing electrical shock thereto.

It is a particular objective of the invention to provide a blood-flow probe, the individual plate temperatures of which may be independently monitored.

It is of most significance of the invention to provide a blood-flow probe having a hot plate which is incapable of heating to a temperature in excess of 42° C.

SUMMARY OF THE INVENTION

In its preferred embodiment, the blood-flow probe of the present invention utilizes two two-terminal integrated circuit temperature transducers each of which produces an output current proportional to the absolute temperature of the probe contact plate with which the temperature transducer is associated. One such temperature transducer monitors the temperature of the cold plate of the probe. The other temperature transducer monitors that of the hot plate. Each transducer output signal is carried from the probe so that the temperature of the hot plate and of the cold plate may be independently measured. Each of these signals is then input to a differential amplifier such that a differential temperature signal may be made available to a conventional monitoring device. The signal output by the temperature transducer monitoring the hot plate of the probe is also input to a comparator where its level is compared with a reference signal indicative of a hot plate temperature on the order of 42° C. Should the hot temperature exceed the temperatures associated with the reference signal, then the comparator output will cause the Peltier Stack Heat Pump of the probe to be de-energized until such time as the hot plate temperature is reduced to a safe level which will not endanger the patient whose blood-flow is being monitored. Additional features of the invention provide that both the hot and cold contact plates of the blood-flow probe shall be at ground potential to eliminate electrical shock hazards. The material in which the probe is housed as well as the sheathing of the signal cables from the probe to the monitoring equipment is selected of material which is known not to damage bodily tissues.

DESCRIPTION OF THE DRAWINGS

FIG. 1 is a block diagram illustrating the blood-flow probe of the invention and the assoicated electrical components which in association with the subject blood-flow probe permit near real time monitoring of blood-flow at the operative site with minimal danger to the patient by the introduction there of the subject blood-flow monitoring probe.

FIGS. 2 and 3 suggest the structural configuration of the hot and cold plates of the blood-flow probe which are placed in contact with the bodily tissue at the operative site so as to monitor blood-flow conditions there.

DESCRIPTION OF THE INVENTION

FIG. 1 illustrates blood-flow probe 10 and the components associated therewith. Monitor 11 may be considered as conventional auxiliary equipment useful in recording the differential temperature of the hot and cold plates of probe 10. For example, monitor 11 may be a Grass Model 7 polygraph manufactured by the Grass Instrument Company of Quincy, Massachusetts.

Probe 10 consists of a thermoelectric heat pump such as Marlow Industries MI 1020. Coupled to heat pump 101 is a heat dissipating plate 102, the hot plate, and a heat absorbing plate 103, the cold plate. Associated with each plate, 102 and 103, is a temperature transducer, 104 and 105 respectively. Temperature transducers 104 and 105 may be comprised of Analog Devices AD 590 temperature transducers. The AD 590 is basically a proportional to absolute temperature (PTAT) current regulator. That is, the output current is equal to a scale factor times the temperature of the sensor in degrees Kelvin. The device particularly lends itself to remote sensing applications such as experienced here when using the probe to measure blood-flow through bodily tissue adjacent to an operative site. Since the AD 590, or its equivalent, provides a high impedance current output, the device is insensitive to voltage drops over long lines. Any well-insulated wire pair is sufficient to carry the output signal of temperature transducers 104 and 105 hundreds of feet to the associated componentry. Since the output is a current rather than a voltage, excellent rejection of interference signals results. Further, the high output impedance of the device, in excess of ten magohms, provides excellent rejection of supply voltage drift and ripple.

To assure stability of heat pump 101, it is powered by means of constant current source 12, which may comprise current regulator MC 1566 manufactured by Motorola, Inc. Hot and cold plates 102 and 103, respectively, while thermally coupled to heat pump 101 are electrically isolated therefrom. Further, to reduce the possibility of shock hazard to the patient, plates 102 and 103 and their connection with temperature transducers 104 and 105 respectively, are maintained at powerline ground potential.

A signal proportional to the absolute temperature sensed at cold plate 103 by temperature transducers 105 is passed through amplifier 13 from whence it is provided to a monitoring output 131 and to the input of differential amplifier 15. Temperature transducer 104 senses the temperature of hot plate 102 and provides an output signal proportional to the absolute temperature of hot plate 102 to amplifier 14. This amplified "hot" signal is provided to monitoring port 141 and to a second input of differential amplifier 15. The output of differential amplifier 15 is the differential temperature of hot plate 102 and cold plate 103, indicated in FIG. 1 as (H-C).

An advantage of the instant invention over prior art devices is now readily apparent. Prior art devices made use of temperature sensing thermocouple devices connected in such a manner that the output of blood-flow probe 10 was a differential temperature. With prior art devices it was impossible to determine the actual temperature of either the hot or the cold plate. With the instant invention the hot and the cold temperature may be determined by monitoring sampling ports 141 and 131 respectively. Further, in prior art devices it was impossible to sense the ambient temperature of the bodily tissue on which hot and cold plates 102 and 103 were placed in contact. It is easily understood that when heat pump 101 is de-energized, contact plates 102 and 103 will quickly assume the ambient temperature of the bodily tissue in contact therewith. Thus, when heat pump 101 of the present invention is de-energized, the signal presented at monitoring ports 131 and 141 will be proportional to the ambient absolute temperature of the bodily tissues in contact with plates 102 and 103.

The differential temperature signal, H-C, is fed from differential amplifier 15 to the input of any suitable monitor 11. At monitor 11 the actual blood-flow characteristics at site of blood probe 10, within the response time limits of the probe, may be monitored and compared with known blood flow characteristics derived from radioactive diffusion-washout measurements. In addition, within 4.2 seconds, the response time of the probe, any pertubations in blood-flow through the tissues or organ at the operation site will be made readily apparent to one observing monitor 11 so that necessary modifications in operative procedure may be immediately undertaken.

Though prior workers in the field believed the relationship between blood-flow and differential temperature to be a linear one and sought to restrain the data obtained to a linear response I have determined that, in actuality, an inverse relationship appears to hold.

Assume the blood-flow probe is being used to monitor a brain near the site of a surgical procedure. Given the following definitions:

Pin = Power into the Peltier stack;
Tn = Temperature of hot plate;
Tc = Temperature of Cold plate;
Tb = Temperature of tissue or organ surface;
Qd = Power dissipated from hot plate;
Qa = Power absorbed from cold plate;
Sf = A standardization factor;
K = Thermal conductivity of the tissue or organ.

the following relationships, which are known in the art may be derived:

$$Pin = Qd - Qa = SfK(Th + Tc - 2Tb)$$

$$\frac{Qd}{SfK} = Th - Tb, \text{ and} \quad (1)$$

$$\frac{Qa}{SfK} = Tb - Tc. \text{ Thus,} \quad (2)$$

$$\frac{Qd + Qa}{SfK} = Th - Tc, \text{ and} \quad (3)$$

$$\frac{Qd + Qa}{Sf} = K(Th - Tc). \quad (4)$$

According to Grason the thermal conductivity, K, of tissue may be defined as $$K = Ko + iQf \quad (5)$$

where Ko is the conductivity of the tissue or organ with zero blood-flow (the "dead organ" conductivity) and iQf is the incremental change in thermal conductivity due to an incremental change in flood flow.

Thus equation (4) may be rewritten as:

$$\frac{Qd + Qa}{Sf} = (Ko + iQf)(Th - Tc) \quad (7)$$

It may be demonstrated that the maximum differential temperature, $\Delta Tmax$, of the hot and cold plates occurs during conditions of zero blood flow (Qf=0) when the thermal conductivity of the organ is Ko, the dead organ conductivity. Applying these facts to equation (7) yields:

$$\frac{Qd + Qa}{Sf} = Ko \, \Delta Tmax \quad (8)$$

Recognizing the identities set forth in equations (7) and (8) permits one to write:

$$Ko \, \Delta Tmax = (Ko + iQf)(Th - Tc). \quad (9)$$

The expression for blood flow, Qf, may now be derived as $$Qf = \frac{Ko}{i}\left(\frac{\Delta Tmax}{Th - Tc} - 1\right) \quad (10)$$

The dead organ conductivity, Ko, the maximum differential temperature $\Delta Tmax$, and the incremental coefficient, i, will, in general, be known and constant. The incremental coefficient, i, is related directly to the Xenon washout test. Thus, the only variable factor affecting blood flow determination is the differential temperature, Th−Tc.

Equation (10) indicates that rather than exhibiting a linear relationship to blood flow, the differential temperature, Th−Tc, is actually inversely proportional to blood flow. Knowledge of this factor will enable closer correlation of blood flow probe measurement results with those obtained by radioactive diffusion-washout.

To further enhance the safe use capabilities of probe 10, the signal proportional to the absolute temperature of hot plate 102 is passed from amplifier 14 to an input of comparator 16 where this hot temperature signal is compared with a reference signal applied to a second input of said comparator 16. Since tissue damage is known to occur at temperatures in excess of 42° C., the reference signal may be a signal proportional to an absolute temperature on the order of that limiting temperature, 42° C. When the temperature signal associated with hot plate 102 exceeds the reference temperature signal the output of comparator 16 causes heat pump 101 to be de-energized in a manner now to be discussed.

Constant current source 12 drives heat pump 101. Current source 12 is powered by power supply 17. An output of power supply 17 is provided to energize relay coil 18 through optical coupler 19 to the ground side of power supply 17. When relay coil 18 is so energized, normally open contacts 181 close. This closure of contacts 181 permits current source 12 to drive heat pump 101. When an output signal from comparator 16 indicates that the signal proportional to the temperature of hot plate 102 has exceeded the reference temperature signal, this comparator output signal is applied to optical coupler 19 to break the conduction path through relay coil 18. With the conduction path through relay coil 18 broken, contacts 181 in turn open, breaking the conduction path from current source 12 to heat pump 101 and thereby de-energizing the heat pump. With the heat pump de-energized the temperature of hot plate 102 will decrease toward the ambient temperature of the tissue or organ with which plate 102 is in contact. The output of comparator 16 may be observed at monitoring port 161 to supply the means for providing a visual or audible alarm indicative of the temperature status of hot plate 102. In this manner, therefore, the temperature of plate 102 will never exceed the safe limit established by the reference signal applied to comparator 16; and any perturbations caused in the blood flow presentation on monitor 11, as a result of de-energizing heat pump 101, will be readily identifiable through utilization of the alarm signal presented at monitoring port 161.

Amplifiers 13 and 14, differential amplifier 15, and comparator 16, may each comprise one quarter of device MC3403 manufactured by Motorola, Inc. Optical coupler 19 may be comprised of device 4N25 manufactured by Motorola, Inc.

Probe 10 will have an overall diameter on the order of one-half inch with an overall thickness of approximately a quater of an inch. Contact plates 102 and 103 are illustrated in greater detail in FIGS. 2 and 3. In the plan view of FIG. 2, each of these plates appears generally semi circular while the elevation of FIG. 3 shows them to have an L-shaped cross section. The radius of curvature R is generally that of the overall probe, on the order of 0.25 inches. The probe is provided in a small package so as to minimize obstruction of the operative field. A small wire harness carries the signal from the probe a convenient distance to the components associated with the processing of the signals output by the probe. The materials used in the construction of the probe and in sheathing the signal cable are selected for their compatibility with human tissue. Thus, gold contact plates are used for hot and cold plate 102 and 103 respectively. The probe housing is made of a two-part resin and hardener such as is used to incapsulate pacemakers for implantation in the human body. The signal cable from the probe is sheathed in a silicon rubber, known not to damage bodily tissues.

When consideration is given to the care employed in selecting tissue-compatible material in constructing the probe and cable sheath; as well as to the performance characteristics of the blood-flow probe which allow monitoring of individual hot and cold plate temperatures, the ambient temperature of the tissue in contact with the probe, the monitoring of the hot plate temperature against a selected-to-be-safe reference with subsequent deactivation of the heat pump should the hot plate exceed that safe reference; and with the care employed to maintain the contact plates at the ground potential of the sixty Hertz powerline it is obvious that a significantly improved thermodiffusion blood-flow probe has been provided which far surpasses the capability and safe operating limits of prior art devices. While the invention has been particularly shown and described in reference to a preferred embodiment thereof, it will be understood by those skilled in the art that suitable modification may be made without departing from the spirit and scope of the invention.

For example, an alternate embodiment might omit the heat pump and provide only a hot plate and a neutral plate (neither heated nor cooled except as affected by the ambient temperature). For use on the brain which has a normal temperature of 37° C., too small a differential temperature range would be available for accurate measurements since the hot plate could not be raised too much without approaching the critical 42° C. temperature. The use of a heat pump is preferred because of the greater differential temperatures available.

Another alternate embodiment might use a cold plate and a neutral plate. Here there would be problems of heat dissipation to eliminate heat absorbed by the cold plate. The needs for cooling fins or water cooling would compound problems of maintaining small probe size and sterile site conditions.

It is possible also to maintain a constant differential temperature at the probe and monitor the current drive to the heat pump, since, it can be shown, there is a linear relationship between blood-flow and the square of the current ($I^2$). Here it would be mandatory that hot plate temperatures be monitored since a patient with a temperature could cause the absolute temperature of the hot plate to rise because of the maintenance of a constant temperature at the plates.

It may even be shown that blood flow may be determined by monitoring the three temperatures Th, Tc, and Tb. The basic consideration of all the approaches is that there be a determination of at least two temperatures or the difference between them. One of said temperatures being higher than the other is referred to herein as the hot plate temperature. This reference would hold even if the embodiment were that in which one plate were actively cooled and the other maintained neutral. In such an instance, the neutral plate would be the "hot plate" defined herein.

An analogous statement might be made with respect to the cold plate in a system in which one plate is actively heated and the other (the "cold plate") was maintained neutral, i.e. at ambient temperature. In all the alternatives offered, that disclosed in full herein is deemed preferable for its ease of use, accuracy and safety.

Having described my invention in such clear and concise terms, both in the text and the drawings associated therewith, that one skilled in the art may simply and easily practice the invention, that which I claim is:

1. In a thermodiffusion blood-flow probe system comprising a thermodiffusion probe having a hot and a cold body-tissue-contact plate wherein the temperature gradient between said plates is independent of ambient body-tissue temperature but varies with blood flow through said body tissues the improvement comprising:
    (a) first signal means coupled to said hot contact plate for outputting a signal proportional to the temperature of said hot plate;
    (b) second signal means coupled to said cold contact plate for outputting a signal proportional to the temperature of said cold plate;
    (c) reference signal means for outputting a signal proportional to a selected safe temperature to which body tissue may be exposed without damage while said probe is used to determine blood flow; and
    (d) comparison means for comparing the relative level of the output of said reference signal means and the output of said first signal means.

2. The system of claim 1 wherein said first signal means is a semiconductor device.

3. The system of claim 1 wherein said second signal means is a semiconductor device.

4. The system of claim 2 wherein said semiconductor device is an integrated circuit temperature transducer.

5. The system of claim 3 wherein said semiconductor device is an integrated circuit temperature transducer.

6. The system of claim 1 further comprising means for determining a change in the relative levels of said signal proportional to said hot plate and said signal proportional to said cold plate.

7. The system of claim 6 wherein said change determining means comprises:
    (a) a first input port coupled to the output of said first signal means;
    (b) a second input port coupled to the output of said second signal means; and
    (c) an output port for outputting a signal proportional to any change in the relative levels of signals output by said first and second signal means.

8. The system of claim 7 wherein said change determining means is a differential amplifier.

9. The system of claim 7 further comprising means for monitoring the signal output from change determining means.

10. The system of claim 1 wherein said comparison means comprises a comparator having:
(a) a first input port coupled to said reference signal means;
(b) a second input port coupled to said first signal means; and
(c) an output port for outputting a signal determinative of the fact that the signal input to said second input port of said comparator has exceeded the limit established by the reference signal input to said first input port of said comparator.

11. The system of claim 10 further comprising a monitoring port coupled to the output port of said comparator.

12. The system of claim 10 having reaction means to effect a change in temperature of the said hot contact plate in response to said signal output by said comparator.

13. The system of claim 12 having a thermoelectric heat pump coupled to said hot and said cold contact plates.

14. The system of claim 13 having power supply means coupled to said heat pump for providing the necessary drive to power said heat pump.

15. The system of claim 14 having means for controlling the coupling of said power supply means to said heat pump being responsive to said reaction means so as to control the application of said drive to said heat pump.

16. The system of claim 12 having ground coupling means for maintaining said hot and said cold contact plates at primary power line ground potential.

17. The system of claim 10 having a thermoelectric heat pump coupled to said hot and said cold contact plates.

18. The system of claim 10 having ground coupling means for maintaining said hot and said cold contact plates at primary power line ground potential.

19. The system of claim 1 having a thermoelectric heat pump coupled to said hot and said cold contact plates.

20. The system of claim 1 having ground coupling means for maintaining said hot and said cold contact plates at primary power line ground potential.

21. The system of claim 1 wherein said probe has body means fabricated of materials known to be compatible with body tissue so as to cause no tissue damage while in use.

22. The system of claim 1 further comprises signal transmission means for conveying signals from said probe to various associated monitoring ports and devices.

23. The system of claim 22 wherein said transmission means comprises electrical conductors.

24. The system of claim 23 wherein said electrical conductors are sheathed in materials known to be compatible with body tissue so as to cause no tissue damage while said probe is in use.

25. In a thermodiffusion blood flow probe system comprising a thermodiffusion probe having a hot and cold body-tissue-contact plate wherein the temperature gradient between said plates is independent of ambient body-tissue temperature but varies with blood flow through said body tissue, the improvement comprising:
(a) first signal means coupled to said hot contact plate for outputting a signal proportional to the temperature of said hot plate;
(b) second signal means coupled to said cold contact plate for outputting a signal proportional to the temperature of said cold plate; and
(c) monitoring means coupled to at least one of said first and second signal means for monitoring at least one of said signal output by said first and second signal means.

* * * * *